United States Patent [19]

Avens et al.

[11] Patent Number: 5,166,324

[45] Date of Patent: Nov. 24, 1992

[54] ACTINIDE HALIDE COMPLEXES

[75] Inventors: Larry R. Avens, Los Alamos; Bill D. Zwick, Santa Fe; Alfred P. Sattelberger, Los Alamos; David L. Clark, Los Alamos; John G. Watkin, Los Alamos, all of N. Mex.

[73] Assignee: The United States of America as represented by the United States Department of Energy, Washington, D.C.

[21] Appl. No.: 651,864

[22] Filed: Feb. 7, 1991

[51] Int. Cl.$^5$ ............................................... C07F 5/00
[52] U.S. Cl. .................................................... 534/11
[58] Field of Search ........................................ 534/11

[56] References Cited

PUBLICATIONS

Brown et al., J. Chem. Soc. A, (3) pp. 476-480, 1970, CA 72:74165r.
Karraker et al., Inorg. Chem., 19(11), pp. 3545-3547, 1980, CA 93:196843q.
Brown et al., Inorg. Syn. 1970, vol. 12, 225-232, CA 37915f, vol. 74.
Molodkin et al. Zh. Neorg. Khim., 1970, 15(12), 3245-3248, CA 60334z, vol. 74.
Srivastava et al., J. Inorg. Nucl. Chem., 1981, 43(6), 1393-1395, CA 95:143282r.
Alvey et al., J. Chem. Soc., Dalton Trans., 1973, (21), pp. 2326-2330.
Clark et al. Inorganic Chemistry, vol. 28, pp. 1771-1773 (1989).
Deacon et al., Polyhedron, vol. 7, pp. 249-250 (1988).
Karraker et al., Inorganic Chimica Acta, vol. 139, pp. 189-191 (1987).
Asprey et al., Inorganic Chemistry, vol. 3, pp. 1137-1440 (1964).
Du Preez et al., Inorganica Chimica Acta, vol. 118, pp. L25-26 (1986).
Suleimanov et al., Journal of Organometallic Chemistry, vol. 235, pp. (C19-C20) (1982).
Suleimanov et al., Doklady Chemistry English Translations, pp. 254-258 (1983).
Imamoto et al., Chemistry Letters, pp. 501-502 (1987), disclose the use of elemental iodine for dissolving a lanthanide, e.g., samarium, in tetrahydrofuran.

Primary Examiner—Robert L. Stoll
Assistant Examiner—C. Sayala
Attorney, Agent, or Firm—Bruce H. Cottrell; Paul D. Gaetjens; William R. Moser

[57] ABSTRACT

A compound of the formula $MX_nL_m$ wherein M is a metal atom selected from the group consisting of thorium, plutonium, neptunium or americium, X is a halide atom, n is an integer selected from the group of three or four, L is a coordinating ligand selected from the group consisting of aprotic Lewis bases having an oxygen-, nitrogen-, sulfur-, or phosphorus-donor, and m is an integer selected from the group of three or four for monodentate ligands or is the integer two for bidentate ligands, where the sum of n+m equals seven or eight for monodentate ligands or five or six for bidentate ligands, a compound of the formula $MX_n$ wherein M, X, and n are as previously defined, and a process of preparing such actinide metal compounds including admixing the actinide metal in an aprotic Lewis base as a coordinating solvent in the presence of a halogen-containing oxidant, are provided.

8 Claims, No Drawings 5,166,324

ACTINIDE HALIDE COMPLEXES

FIELD OF THE INVENTION

The present invention relates to the field of organometallic chemistry and actinide processing. This invention is the result of a contract with the Department of Energy (Contract No. W-7405-ENG-36).

BACKGROUND OF THE INVENTION

A wide variety of organometallic compounds are constantly developed to provide additional synthetic routes to other compounds of selected metals. The synthetic chemistry of actinide metals is of particular interest as it may yield new methods for environmental controls or clean-up of such metals as well as provide improved synthetic routes to both known and new compounds of such metals.

Clark et al. disclose, in Inorganic Chemistry, vol. 28, pgs. 1771-1773 (1989), uranium triiodide adducts. There was no suggestion of applying this chemistry to actinide metals, other than uranium.

Karraker et al. disclose, in Inorganica Chimica Acta, 139, pgs. 189-191 (1987), the reaction of diiodoethane with the actinide metals neptunium and plutonium in tetrahydrofuran as a solvent to yield the respective metal iodine tetrahydrofuran complex. Such a method has been previously reported for the lanthanide metals samarium and ytterbium (see, Girard et al., JACS, 102, 1980, 2693). Problems with the Karraker et al. process include the use of diiodoethane, a known carcinogen, and the evolution of ethylene, a flammable gas. Karraker et al. further disclose that their process does not work with, e.g., thorium and uranium metals.

Deacon et al. disclose, in Polyhedron, 7, pgs. 249-250 (1988), the reaction of uranium with mercuric halides, specifically the chloride or iodide, in boiling tetrahydrofuran to yield a uranium halide tetrahydrofuran complex. A problem with this process is that a very large excess of uranium metal must be used to form the uranium trihalide as elemental mercury formed in the reaction forms an unreactive amalgam with uranium metal.

Asprey et al. disclose, in Inorg. Chem., 3, pgs. 1137-1140 (1964), the reaction of lanthanide metals with mercuric halides at high temperatures in a tube furnace to yield anhydrous lanthanide trihalides.

It is an object of this invention to provide novel organometallic compounds of actinide metals such as thorium, plutonium, neptunium and americium.

It is a further object of this invention to provide a convenient low temperature synthesis of actinide halides from actinide metals such as thorium, plutonium, neptunium and americium by the intermediate formation of organometallic compounds of such actinide metals.

SUMMARY OF THE INVENTION

To achieve the foregoing and other objects, and in accordance with the purposes of the present invention, as embodied and broadly described herein, the present invention provides a compound of the formula $MX_nL_m$ wherein M is an actinide metal atom, selected from the group of thorium or americium X is a halide atom, n is an integer selected from the group of three or four, L is a coordinating ligand selected from the group consisting of aprotic Lewis bases having an oxygen-, nitrogen-, sulfur-, or phosphorus-donor, and m is an integer selected from the group of three or four for monodentate ligands or is two for bidentate ligands, where the sum of n+m equals seven or eight for monodentate ligands or five or six for bidentate ligands and a compound of the formula $MX_nL_m$ wherein M is an actinide metal atom selected from the group consisting of plutonium or neptunium, X is a halide atom, n is an integer selected from the group of three or four, L is a coordinating ligand selected from the group consisting of pyridine, acetonitrile, dimethyl sulfoxide, or 1,2-dimethoxyethane, and m is four for pyridine, acetonitrile, or dimethyl sulfoxide, or is two for 1,2-dimethoxyethane. The present invention further provides a process for preparing the actinide metal compounds or complexes of the formula $MX_nL_m$, wherein M, X, n, L, and m are as previously defined, said process including admixing the actinide metal in an aprotic Lewis base having an oxygen-, nitrogen-, sulfur-, or phosphorus-donor as a coordinating solvent, in the presence of a halogen-containing oxidant, such process preferably conducted at temperatures at or below room temperature. Finally, the present invention provides a process for the low temperature preparation of actinide halide compounds of the formula $MX_x$ wherein M is a metal atom selected from the group consisting of thorium, plutonium, neptunium or americium, X is a halide atom, and x is an integer selected from the group of three or four, the process including heating a compound of the formula $MX_nL_m$ wherein M is an actinide metal atom, X is a halide atom, n is an integer selected from the group of three or four, L is a coordinating ligand selected from the group consisting of aprotic Lewis bases having an oxygen-, nitrogen-, sulfur-, or phosphorus-donor, and m is an integer selected from the group of three or four for monodentate ligands or is two for bidentate ligands, where the sum of n +m equals seven or eight for monodentate ligands or five or six for bidentate ligands, at temperatures and for time sufficient to form the actinide halide compounds.

DETAILED DESCRIPTION

The present invention concerns novel organometallic compounds or complexes of the actinide metals thorium, plutonium, neptunium or americium.

The present invention provides a compound of the formula $MX_nL_m$ wherein M is an actinide metal atom, X is a halide atom, n is an integer selected from the group of three or four, L is a neutral coordinating ligand selected from the group consisting of aprotic Lewis bases having an oxygen-, nitrogen-, sulfur-, or phosphorus-donor, and m is an integer selected from the group of three or four for monodentate ligands or is the integer two for bidentate ligands, where the sum of n+m equals seven or eight for monodentate ligands or five or six for bidentate ligands. Such actinide halide ligand compounds can be used as intermediates in the low temperature preparation of the corresponding actinide halide, may be used for synthesis of other actinide compounds, or may be used in a separation process for the separation of such actinide metals from other non-actinide metals.

The aprotic Lewis bases used in the present invention have an oxygen-, nitrogen-, sulfur-, or phosphorus-donor, more preferably an oxygen-, or nitrogen-donor. Among suitable aprotic Lewis bases having an oxygen-, nitrogen-, sulfur-, or phosphorus-donor are included tetrahydrofuran, pyridine, acetonitrile, dimethyl sulfoxide, and 1,2-dimethoxyethane, and may include amines such as, e.g., trimethyl amine or triethyl amine, phosphines such as, e.g., trimethyl phosphine or triethyl phosphine, ethers, preferably high boiling ethers such as, e.g., n-butylether, and thioethers, e.g., tetrahydrothiophene.

Suitable halide atoms can include chlorine, bromine, and iodine with bromine and iodine being especially preferred.

The process for preparing the actinide metal compounds or complexes of the formula $MX_nL_m$, wherein M, X, n, L, and m are as previously defined, involves admixing the actinide metal in an aprotic Lewis base having an oxygen-, nitrogen-, sulfur-, or phosphorus-donor, as a coordinating solvent, in the presence of a halogen-containing oxidant for time and at temperatures sufficient to produce the compound. The halogen-containing oxidant can be an elememtal halogen such as chlorine, bromine or iodine or may be a hypochlorite such as calcium hypochlorite or an organic halide such as a methyl halide, or dihaloethane. Generally, the reaction can be conducted at any convenient temperature, although preferably the reaction is conducted at temperatures at or below room temperature, i.e., at or below about 20° C., to obtain the best yields.

Generally, the process involves dispersing the actinide metal in a large excess of the aprotic Lewis base and slowly adding a stoichiometric amount of an elemental halogen to the admixture. Addition of the halogen is continued and reaction allowed to continue until completion is indicated when an assay shows complete consumption of the actinide metal. The resultant product will be either a precipitate or a dissolved species depending upon the selection of actinide metal and ligand, and the amount of aprotic Lewis base present for solvation. Such a precipitated species can be separated or isolated by filtration. When the product is a dissolved species, the solution is generally filtered to remove unwanted suspended materials and the excess solvent or aprotic Lewis base removed under reduced pressure to yield the crystalline product.

The process for preparing the actinide halide compounds of the formula $MX_x$, wherein M, X, and x are as previously defined, involves heating a compound of the formula lu $MX_nL_m$ wherein M is an actinide metal atom, X is a halide atom, n is an integer selected from the group of three or four, L is a coordinating ligand selected from the group consisting of aprotic Lewis bases having an oxygen-, nitrogen-, sulfur-, or phosphorus-donor, and m is an integer selected from the group of three or four for monodentate ligands or is two for bidentate ligands, where the sum of n+m equals seven or eight for monodentate ligands or five or six for bidentate ligands, at temperatures and for time sufficient to form the actinide halide compounds. Generally, heating can be conducted at temperatures from about 100° C. to about 200° C. for periods of time from about 1 hour to about 10 hours. This process of converting the actinide halide ligand complexes into actinide halides is accomplished at substantially lower temperatures than those temperatures required in previous high temperature, i.e., about 800° C., tube furnace preparations. As the conversion of actinide metal to the actinide halide ligand complexes is also carried out at low temperatures, preferably at temperatures at or below room temperature (about 20° C.), the present invention allows for the conversion of actinide metal to the actinide halide without the need for high energy consumptive temperatures.

The majority of starting materials used and products formed in the present invention are extremely moisture and oxygen sensitive. Accordingly, such materials and products should be handled under an inert atmosphere of oxygen-free nitrogen, argon or helium. Solvents used in the process should be similarly free of oxygen and water.

The present invention is more particularly described in the following examples which are intended as illustrative only, since numerous modifications and variations will be apparent to those skilled in the art.

Neptunium and plutonium compounds of the present invention were handled in a radiation-containment glove box under a helium atmosphere.

NMR spectra for neptunium and plutonium were recorded at ambient room temperature on an IBM 250 spectrometer.

NMR spectra for thorium were recorded at ambient room temperature on a Bruker EM 300 spectrometer. All $^1$H NMR, impurity in benzene-d6 set at 7.15 ppm or toluene-$d_8$ set at 2.09 ppm.

Infrared spectra for neptunium and plutonium were recorded as nujol mulls between KBr plates which were placed in a spectroscopy well (fitted with Irtran-44 windows) attached to the radiation-containment glove box and mated to an IBM 32 optics bench.

Infrared spectra for thorium were recorded on a Bio-Rad Digilab FTS-40 spectrophotometer interfaced with a 3240 SPC computer.

Thermogravimetric analyses (TGA) were recorded on a Perkin-Elmer 7-Series Thermogravimetric Analyzer in a glove box with the furnace under an argon purge.

Elemental analysis was conducted on a Perkin-Elmer 2400 CHN analyzer.

EXAMPLE 1

A one liter (L) Schlenk reaction vessel with a Teflon-coated magnetic stir bar was charged with 51 grams (g) of thorium turnings. The vessel was attached to a vacuum manifold on a conventional Schlenk vacuum line and the vessel evacuated to $10^{-3}$ Torr and refilled with argon. The evacuate/refill process was repeated two more times and then 400 milliliters (ml) of tetrahydrofuran (THF) was added. Elemental iodine, 90 g, was slowly added to the thorium metal turnings in 12–15 g batches. After addition of each aliquot of iodine, the reaction vessel was shaken vigorously. During this time, the iodine color was slowly discharged and accompanied by the evolution of heat as evidenced by the warmth of the reaction vessel. An ice-water bath was used to maintain the reaction temperature at or near room temperature. After the final aliquot of iodine was added, enough metal turnings had dissolved to allow for magnetic stirring. The solution was allowed to stir at room temperature for 8 hours to yield a pale brown solution with excess metal present both in the form of unreacted turnings and as a dark-grey powder. The reaction vessel was taken into an inert atmosphere glovebox and the solution filtered through a one-inch pad of Celite on a medium frit to give a clear pale-orange solution. The Celite pad and the glassware were washed with three 20-ml portions of THF until the washings were colorless. The solvent was removed in vacuo to leave a sticky off-white solid. Hexane, 400 ml, was added, the sticky solid broken apart with a spatula, and the mixture allowed to stand at room temperature. After 12 hours, large clumps of an off-white brittle solid remained. These solid clumps were ground up using a mortar and pestle, and remaining hexane removed in vacuo. This produced 147 g (80.6 percent yield based upon iodine) of analytically pure $ThI_4(THF)_4$, based upon NMR, TGA and elemental analysis.

EXAMPLE 2

Thorium turnings, 39 g, were broken into 1 inch strips and placed into a 500 ml Schlenk reaction vessel with a one-inch Teflon-coated magnetic stir bar. The vessel was attached to a vacuum manifold on a conventional Schlenk vacuum line and the vessel evacuated to $10^{-1}$ Torr and refilled with argon. The evacuate/refill process was repeated two more times and then 250 ml of THF was added. Using a disposable syringe, elemental bromine, 50 g, was added slowly to the metal in 2–3 ml portions with vigorous stirring. A very exothermic reaction took place as the red color of elemental bromine was discharged. An ice-water bath was used to maintain the reaction temperature between about 30° to 35° C. The dissolution of the thorium metal was accompanied by the slow precipitation of an off-white microcrystalline precipitate. After color from the final addition of bromine had been discharged, there was a mixture of off-white microcrystalline precipitate and a grey powder of elemental thorium in a pale brown solution. The reaction vessel was taken into an inert atmosphere glovebox and the reaction mixture was heated to about 50° C. until all the white precipitate had been dissolved. The hot mixture was vacuum filtered through Celite on a coarse frit to give a pale-yellow filtrate. The Celite pad and the glassware were washed with three 20-ml portions of THF until the washings were colorless. The filtrate volume was reduced to 100 ml at which time a large amount of white microcrystalline solid had precipitated. Hexane, 250 ml, was added to the filtrate with stirring to precipitate the remainder of the product. The white crystalline product was allowed to settle, the supernatant liquid decanted, and the white microcrystalline product dried in vacuo to yield 84 g (70 percent based on bromine) of analytically pure $ThBr_4(THF)_4$, based upon NMR, TGA and elemental analysis.

EXAMPLE 3

Thorium turnings, 7.0 g, were broken into 1 inch strips and placed into a 250 ml Schlenk reaction vessel with a Teflon-coated magnetic stir bar. The vessel was attached to a vacuum manifold on a conventional Schlenk vacuum line and the vessel evacuated to $10^{-3}$ Torr and refilled with argon. The evacuate/refill process was repeated two more times and then 100 ml of acetonitrile was added. Elemental iodine, 11.5 g, was added slowly to the stirred metal suspension in two portions. As the metal dissolution progressed, the initial red-brown color of the iodine solution began to lighten and a pale-yellow microcrystalline precipitate was slowly deposited. After the second portion of iodine had been added, the solution was allowed to stir at room temperature. After 48 hours of stirring, a yellow-brown precipitate was present in a red-brown solution. The reaction vessel was taken into an inert atmosphere glovebox and the mixture was filtered through Celite on a medium frit. The precipitate was washed with hexane, 25 ml, and then dried in vacuo to yield 16.1 g (79 percent based on iodine) of a microcrystalline, pale brown solid characterized as $ThI_4(NCCH_3)_4$, based upon IR, TGA and elemental analysis.

EXAMPLE 4

Thorium turnings, 7.0 g, were broken into 1 inch strips and placed into a 250 ml Schlenk reaction vessel with a Teflon-coated magnetic stir bar. The vessel was attached to a vacuum manifold on a conventional Schlenk vacuum line and the vessel evacuated to $10^{-3}$ Torr and refilled with argon. The evacuate/refill process was repeated two more times and then 125 ml of 1,2-dimethoxyethane (DME) was added. Elemental iodine, 11.5 g, was added slowly to the stirred metal suspension in three portions. As the metal dissolution progressed, the initial red-brown color of the iodine solution began to lighten and a yellow microcrystalline precipitate was slowly deposited. After the final portion of iodine had been added, the solution was allowed to stir at room temperature. After 48 hours of stirring, a white precipitate was present in a colorless solution. The reaction vessel was taken into an inert atmosphere glovebox and the mixture was filtered through Celite on a medium frit. The white precipitate was washed with hexane, 25 ml, and then dried in vacuo to yield 16.8 g (81 percent based on iodine) of a microcrystalline, white solid characterized as $ThI_4(DME)_2$, based upon NMR, TGA and elemental analysis.

EXAMPLE 5

A reaction vessel equipped with a stir bar was charged with neptunium turnings, 0.21 g, and THF, about 5 ml. Elemental iodine, 0.33 g, was added slowly to the stirred metal suspension, giving a deep red-purple color. The reaction vessel was stoppered and the mixture allowed to stir for 24 hours during which time a finely-divided yellow-orange powder precipitated from solution. The solids were collected on a medium-porosity fritted filter and washed with three 5-ml portions of hexane, followed by drying in vacuo to yield 0.68 g (86 percent based on iodine) of a solid characterized as $NpI_3(THF)_4$, based upon NMR, TGA and IR.

EXAMPLE 6

A reaction vessel equipped with a stir bar was charged with plutonium turnings, 0.72 g, and THF, about 10 ml. Elemental iodine, 1.14 g, was added slowly to the stirred metal suspension. The reaction vessel was stoppered and the mixture allowed to stir for 24 hours during which time an off-white microcrystalline powder precipitated from solution. The solids were collected on a medium-porosity fritted filter and washed with three 5-ml portions of hexane, followed by drying in vacuo to yield 2.51 g (86 percent based on iodine) of a solid characterized as $PuI_3(THF)_4$, based upon IR, TGA and elemental analysis.

EXAMPLE 7

A reaction vessel equipped with a stir bar was charged with plutonium turnings, 0.26 g, and pyridine (Py), about ml. Elemental iodine, 0.4 g, was added slowly to the stirred metal suspension. The reaction vessel was stoppered and the mixture allowed to stir for 24 hours during which time no precipitate was observed. The reaction mixture was filtered, and the solvent removed in vacuo to give a dark brown, oily residue. Vacuum drying of the oily residue yielded 0.94 g (94 percent based on iodine) of a solid characterized as $PuI_3(Py)_4$, based upon IR and TGA.

EXAMPLE 8

A reaction vessel equipped with a stir bar was charged with plutonium turnings and dimethyl sulfoxide (DMSO). Elemental iodine was added slowly to the stirred metal suspension. The reaction vessel was stoppered and the mixture allowed to stir for 24 hours during which time no precipitate was observed. The reaction mixture was filtered, allowing recovery of unreacted plutonium and intractable solids. Solvent was removed under vacuum to give an oily, dark green residue. Vacuum drying of the oily residue yielded 0.54 g (61 percent based on iodine) of an oily, dark green solid characterized as $PuI_3(DMSO)_4$, based upon IR and TGA.

Although the present invention has been described with reference to specific details, it is not intended that such details should be regarded as limitations upon the scope of the invention, except as and to the extent that they are included in the accompanying claims.

What is claimed is:

1. A compound of the formula $MX_nL_m$ wherein M is an actinide metal atom of thorium, X is a halide atom of bromine or iodine, n is four, L is a coordinating ligand selected from the group consisting of tetrahydrofuran or 1,2-dimethoxyethane, and m is four for tetrahydrofuran, or is two for 1,2-dimethoxyethane.

2. The compound of claim 1 wherein L is tetrahydrofuran and X is bromine.

3. The compound of claim 1 wherein L is tetrahydrofuran and X is iodine.

4. The compound of claim 1 wherein L is 1,2-dimethoxyethane and X is iodine.

5. A compound of the formula $MX_nL_m$ wherein M is an actinide metal atom of plutonium, X is a halide atom of iodine, n is three, L is a coordinating ligand selected from the group consisting of tetrahydrofuran, pyridine, acetonitrile, dimethyl sulfoxide, or 1,2-dimethoxyethane, and m is four for tetrahydrofuran, pyridine, acetonitrile, or dimethyl sulfoxide, or is two for 1,2-dimethoxyethane.

6. The compound of claim 5 wherein L is pyridine.

7. The compound of claim 5 wherein L is dimethylsulfoxide.

8. The compound of claim 5 wherein L is tetrahydrofuran.

* * * * *